(12) United States Patent
Manners et al.

(10) Patent No.: US 6,372,873 B1
(45) Date of Patent: Apr. 16, 2002

(54) LINEAR PHOSPHINE-BORANE POLYMERS AND METHODS OF PREPARATION THEREFOR

(76) Inventors: Ian Manners; Hendrik Dorn, both of 80 St. George Street, Toronto, Ontario (CA), M5H 3H6

(*) Notice: Subject to any disclaimer, the term of this patent is extended or adjusted under 35 U.S.C. 154(b) by 0 days.

(21) Appl. No.: 09/541,717

(22) Filed: Apr. 3, 2000

(30) Foreign Application Priority Data

Apr. 1, 1999 (CA) .............................. 2268218

(51) Int. Cl.[7] .................. C08G 79/08; C08G 79/02; C09K 21/04
(52) U.S. Cl. ................. 528/6; 528/4; 528/394; 528/398; 252/601; 423/276; 423/293
(58) Field of Search ................. 528/4, 6, 394, 528/398; 252/601; 423/276, 299

(56) References Cited

U.S. PATENT DOCUMENTS

| | | | | |
|---|---|---|---|---|
| 3,012,076 A | * | 12/1961 | Burg et al. | |
| 3,035,095 A | * | 5/1962 | English | |
| 3,240,807 A | * | 3/1966 | Wagner et al. | |
| 3,240,815 A | * | 3/1966 | Wagner et al. | |
| 3,272,781 A | * | 9/1966 | Goodrow | |
| 3,347,800 A | * | 10/1967 | Goodrow et al. | |

* cited by examiner

Primary Examiner—Robert Dawson
Assistant Examiner—Jeffrey B. Robertson
(74) Attorney, Agent, or Firm—Pillsbury Winthrop LLP

(57) ABSTRACT

Linear backbone phosphorus-boron polymers of the general formula (I):

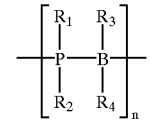

wherein $R_1$, $R_2$, $R_3$, and $R_4$, are the same or different and selected from H, optionally substituted alkyl, alkenyl and phenyl; and n is at least 2, and particularly high molecular weight polymers of absolute weight average molecular weight of at least 10,000. The polymers are of use as fire retardants.

5 Claims, 3 Drawing Sheets

LINEAR PHOSPHINE-BORANE POLYMERS AND METHODS OF PREPARATION THEREFOR

FIELD OF THE INVENTION

This invention relates to novel linear, phosphine-borane polymers, particularly high molecular weight phosphinoborane polymers; methods for the preparation thereof and, particularly, thermally-induced dehydrocoupling methods.

BACKGROUND TO THE INVENTION

Carbon comprises less than 0.1% of the Earth's crust, oceans, and atmosphere. Despite this fact, virtually all polymer systems known and commercially available are based on extended catenated structures containing mainly carbon atoms together with a few other elements, such as oxygen and nitrogen. The availability of suitable organic monomers and the extensive synthetic knowledge associated with organic chemistry allows the design and synthesis of new materials and the subsequent fine-tuning of their properties. In contrast, the development of extended structures based on atoms of other elements has been much less successful and still represents a substantial unsolved synthetic challenge. Nonetheless, the relatively few polymer systems based on inorganic elements such as poly(siloxanes), silicones $[R_2Si-O]_n$, polyphosphazenes $[R_2P=N]_n$, polysilanes $[R_2Si]_n$ and more recently poly(silynes), poly(stannanes), sulfur-containing polymers, poly(metallocenes), and other metallopolymers illustrate the potential for accessing materials with unexpected properties as well as novel applications.

Thermally-induced dehydrocoupling of phosphine-borane adducts $R_2PH.BH_3$ at elevated temperatures of, for example, 150–200° C. has been previously used to prepare cyclic phosphinoborane species, mainly six-membered rings $[R_2P-BH_2]_3$ and, for example, $[R_2P-BH_2]_3$ having considerable thermal and hydrolytic stability.[1] In addition in a few cases, low yields of "polymeric" materials have been made, although none has been structurally characterized and, where reported, the molecular weights were relatively very low.[2] During the early pioneering work in the 1950's and 1960's on boron-phosphorus compounds, the low yield formation of a range of partially characterized, low molecular weight phosphinoborane polymers were described in patents, technical reports and in the academic literature. For example, pyrolysis of $Me_2P-PMe_2.BH_3$ or $RMePH.BH_3$ (R=Me or Et) at 175–200° C. in the presence of amines, which were claimed to promote the formation of linear rather than cyclic products, was reported to give polymers $[RMeP-BH_2]_n$ with molecular weights of 1,800–6,000 (where determined).[2,3] For a general survey of results obtained during this period see G. W. Parshall in "The Chemistry of Boron and its Compounds": E. L. Muetterties Ed., Wiley, N.Y. (1967) Ch. 9 p 617–646. Dehydrocoupling routes to bonds between inorganic elements have provided important routes to Group 14 polymers.[4]

Dehydrocoupling has been used to form oligomers and polymers with B—N bonds between borazine rings,[5] while coordinate bonds between B and N have recently been used in the preparation of metallopolymers.[6]

The phosphine-borane adduct $Ph_2PH.BH_3$ is known to undergo dehydrocoupling at 180–190° C. and above over a period of 14 h to exclusively and quantitatively yield the cyclic trimer $[Ph_2P-BH_2]_3$.[7]

The preparation of very low molecular weight polymers of $M_n$ 1480–2630 from the thermolysis of $PhPH_2.BH_3$ at 150–250° C. in the absence of a catalyst has been described.[8]

PUBLICATIONS

1. C. A. B. Burg and R. I. Wagner, *J. Am. Chem. Soc.* (1953) 75. 3872.
2. R. I Wagner and F. F. Caserio, *J. Inorg. Nucl. Chem.* (1959), 11, 259.
3. A. B. Burg, *J. Inorg. Nucl. Chem.* (1959), 11, 258.
4. See, for example, (a) P. Bianconi, T. W. Weidman *J. Am. Chem. Soc.* (1988), 22, 1697. (b) T. Imori, T. D. Tilley *J. Chem. Soc. Chem. Commun.* (1993), 1607. (c) I. Manners, G. Renner, H. R. Allcock, O. Nuyken *J. Am. Chem. Soc.*, (1989), 111, 5478. (d) J. A. Dodge, I. Manners, G. Renner, H. R. Allcock, O. Nuyken, *J. Am. Chem. Soc* (1990), 112, 1268. (e) M. Liang, I. Manners, *J. Am. Chem. Soc.*, (1991), 113, 4044. (f) A. K. Roy *J. Am. Chem. Soc.* (1992), 114, (g) V. Chunechom, T. E. Vidal, H. Adams, M. L. Turner *Angew. Chem. Int. Ed. Engl.* (1998), 37, 1928.
5. P. J. Fuzan et al. *Chem. Mater.* (1990), 2, 96.
6. M. Fontani et al. *Eur. J. Inorg. Chem.* (1998), 2087.
7. W. Gee et al. *J. Chem. Soc.* (1965), 3171.
8. V. V. Korshak et al. *Izv. Akad. Nauk SSR, Ser. Khim*, (1964), 1541.

SUMMARY OF THE INVENTION

The present invention provides novel, polymeric compounds having a linear backbone of alternating phosphorus and boron atoms.

The invention further provides novel, optionally, metal catalysed dehydrocoupling methods to produce linear phosphorus-boron polymers.

Accordingly, in one aspect the invention provides linear backbone phosphorus-boron polymers of the general formula (I)

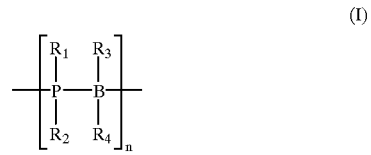

(I)

wherein $R_1$–$R_4$ are the same or different and selected from H, optionally substituted lower alkyl, alkenyl and aryl; and n is at least 2. Preferably, the invention provides a polyphenylphosphinoborane of aforesaid formula (I) wherein $R_1$, H and $R_4$ is phenyl. More preferably, the linear polymers as hereinabove defined included low molecular weight oligomers having weight average molecular weights ($M_w$) of about 5,000 and higher molecular weight polymers having $M_w$ more preferably of at least 10,000, and still more preferably at least 20,000.

In a further aspect, the invention provides a method for producing polymers having a linear backbone of alternating phosphorus and boron atoms, said method comprising dehydrocoupling a phosphine-boron adduct by treating said adduct at a temperature to effect said dehydrocoupling to produce said linear polymer.

Preferably, the aforesaid process is carried out at effective temperatures lower than a temperature which would produce a corresponding phosphorus-boron cyclic trimer compound.

More preferably, the dehydrocoupling methods as hereinabove defined further include the presence of an effective dehydrocoupling catalyst, for example, complexed Rh(I) catalysts or complexes of other metals.

Specific Examples are:
- [Rh(1,5-cod)$_2$][OTf]
- [Rh(PPh$_3$)$_3$Cl]
- [Rh(1,5-cod)(dmpe)][PF$_6$]
- [Rh(CO)(PPh$_3$)$_3$H]
- anhydrous RhCl$_3$
- RhCl$_3$ hydrate
- [{C$_p$*Rh($\mu$Cl)Cl}$_2$]
- [{Ir($\mu$-Cl)Cl}$_2$]
- [Ir(1,5-cod)$_2$][BF$_4$]
- Cp$_2$TiMe$_2$
- Ru$_3$(CO)$_{12}$
- [Pt(1,5-cod)2]
- PdCl$_2$
- PtCl$_2$; and most preferably
- [{Rh($\mu$-Cl)(1,5-cod)}$_2$]

In the foregoing list of compounds, it will be understood that cod represents cyclooctadiene; OTf stands for triflate anion (CF$_3$SO$_2$O$^-$); and Dmpe is dimethylphosphinoethane.

In a further aspect, the invention provides a method of producing the dimer compound of formula I, wherein R$_1$ and R$_2$ are Ph, R$_3$ and R$_4$ are H and n is 2, i.e.

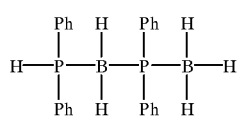
(II)

by treating the phosphine-borane adduct Ph$_2$PH—BH$_3$ at a dehydrocoupling temperature of less than 180° C., preferably in the presence of an effective amount of a dehydrocoupling catalyst.

In alternative methods for producing high molecular weight polymers according to the invention, alkylated derivatives may be made by alkylation of labile hydrogen-bearing phosphorus in the polymers by, for example, reaction with alkylated lithium or Grignard reagents, viz:

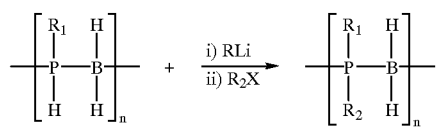

Wherein R$_2$ is an optionally substituted lower alkyl or aryl.

BRIEF DESCRIPTION OF THE DRAWINGS

In order that the invention may be better understood, preferred embodiments will now be described, by way of example only, with reference to the accompanying drawings wherein.

DETAILED DESCRIPTION OF PREFERRED EMBODIMENTS

Synthesis of Dimer (II)

EXAMPLE 1

Figure 1:
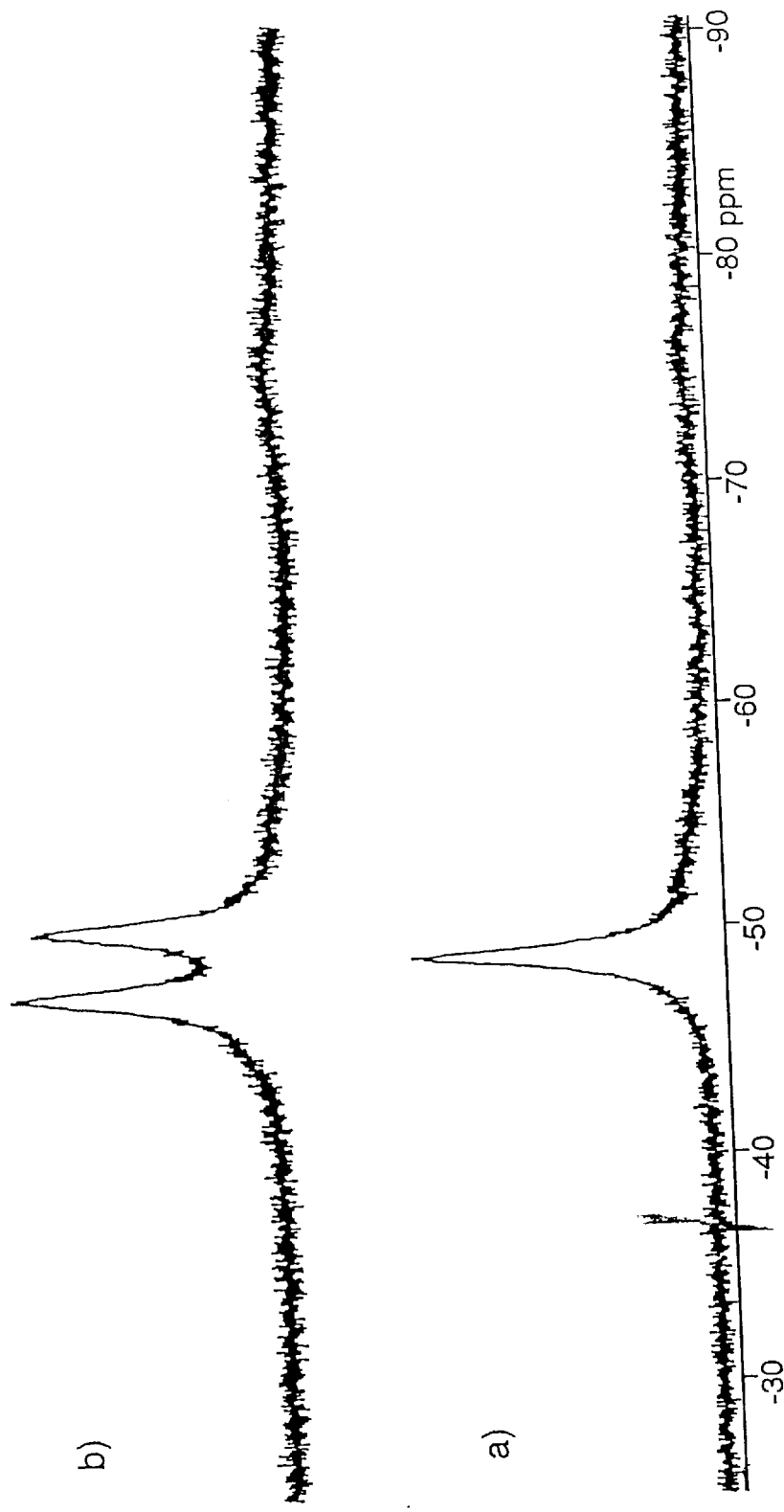
FIG. 1 represents a $^{31}$P NMR spectra of poly (phenylphosphinoborane) (III) (121 MHz) in CDCl$_3$: a) $^1$H decoupled; b) $^1$H coupled, J$_{PH}$=360 Hz.

Neat Ph$_2$PH.BH$_3$. (0.625 g, 3.12 mmol) and [Rh(1,5-cod) $_2$][OTf] (ca. 3 mg, 1 mol %) were heated at 90° C. for 14 h. The reaction mixture became liquid upon heating and solidified when cooled to room temperature. Recrystallization from diethyl ether (10 mL) gave colorless crystals of air-stable compound (II). Yield 0.530 g (85%).

$^1$H NMR (300 MHz, CDCl$_3$): $\delta$=7.68–7.17 (m, 20H, aromatic), 6.71 (d, 1H, J$_{PH}$=397 Hz, PH), 2.24 (br, 2H, BH$_2$), 1.01 (br q, 3H, J$_{BH}$ =75 Hz, BH$_3$); $^{11}$B{$^1$H} NMR (160 MHz, CDCl$_3$): $\delta$=–33.2 (br, BH$_2$), –37.3 (br m, BH$_3$); $^{31}$P{$^1$H} NMR (121 MHz, CDCl$_3$): $\delta$=–3.3 (br m, Ph$_2$PH), –17.7 (br, Ph$_2$P); MS (EI, 70 eV): m/z (%): 395 (16) [M$^+$3H], 384 (100) [M$^+$-BH$_3$].

Crystal data for C$_{24}$H$_{26}$B$_2$P$_2$ (II). orthorhombic P2$_1$2$_1$2$_1$, a=10.247(2), b=13.616(3), c=15.684(3) Å, V=2188.3(7) Å$^3$, Z=4, $\mu$=0.206 mm$^{-1}$, MoK$\alpha$($\lambda$=0.71073 Å), $\rho_{calcd}$=1.208 Mgm$^{-3}$, 150.0(1) K, Nonius KappaCCD with graphite monochromator, colourless crystal (0.28×0.17×0.12 mm). Of 16513 reflections collected (4.18$\leq$θ$\leq$26.36°) 4455 were independent R$_{int}$=0.061, and 3849 were observed with F$_o$$\geq$4$\sigma$(F$_o$). Solution by direct methods and refinement on F$^2$ using SHELXTL-PC V5.1 (Sheldrick, G. M., Bruker AXS Inc., Madison, Wis., USA, 1997), hydrogen atoms attached to C atoms and B(2) were included in calculated positions and treated as riding atoms, hydrogen atoms attached to B(1) and P(2) were refined with anisotropic thermal parameters, R1=0.0342, wR2=0.0820 (R1=$\Sigma$(F$_o$–F$_c$)/$\Sigma$F$_o$ observed data, wR2={$\Sigma$[w(F$_o$$^2$–F$_c$$^2$)$^2$]/$\Sigma$[w(F$_o$$^2$)$^2$] }$^{1/2}$ for all data), GOF=1.059, N$_o$/N$_v$=16.56 and $\Delta\rho_{max}$= 0.283 eÅ$^{-3}$. Cambridge data base CCDC 114009.

There are thermal ellipsoids at the 30% probability level. Selected bond lengths [Å] and angles [°]: P(1)-B(2) 1.932 (2), P(1)-B(1) 1.944(2), P(2)-H(1P) 1.349(19), P(2)-B(1) 1.923(2); B(2)-P(1)-B(1) 113.01(11), H(1P)-P(2)-B(1) 112.6(8), P(2)-B(1)-P(1) 109.23(12).

EXAMPLE 2

Example 1 was repeated, but with Ru$_3$(CO)$_{12}$ substituted for catalyst [Rh(1,5-cod)$_2$][OTf]. A significant, but lower catalytic effect was observed, Synthesis of Poly(phenyl phosphinoborane)(III)

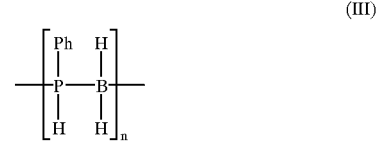
(III)

EXAMPLE 3

Reactions were run under nitrogen. Work up of poly (phenylphosphinoborane) (III) was carried out in air. Gel Permeation Chromatography (GPC) was performed in THF using polystyrene standards for column calibration. (FIG. 2.)

In a series of experiments using ca. 0.1–1 mol % catalyst the molecular weights of the poly(phenylphosphinoborane) (III) formed varied in the range apparent M$_w$=80,000–150, 000 and M$_n$=50,000–90,000. In the largest scale preparation PhPH$_2$.BH$_3$ (1.025 g, 8.27 mmol) and [Rh(1,5-cod)$_2$][OTf]

(ca. 3 mg, 0.1 mol %) were dissolved in toluene (15 mL) and the resulting solution was refluxed for 14 h. The reaction mixture was then concentrated under vacuum to ca. 5 mL, filtered and precipitated into 120 mL of hexanes. The white polymeric product 2 was washed with hexanes, decanted and dried in vacuo. Yield 0.678 g (67%). GPC (THF): major fraction apparent $M_w$=87,270, $M_n$=59,970, PDI=1.46; minor fraction, $M_w$=1,840, $M_n$=1,250, PDI=1.47; $^1$H NMR (300 MHz, CDCl$_3$): δ=6.65–7.90 (br, Ph), 4.25 (br d, $J_{PH}$=360 Hz, PH), 0.67–2.19 (br, BH$_2$); $^{11}$B{$^1$H} NMR (160 MHz, CDCl$_3$): δ=−34.7 (br, s); $^{13}$C{$^1$H} NMR (75 MHz, CDCl$_3$): δ=132.5 (br, o-Ph), 129.3 (br, p-Ph), 128.2 (br, m-Ph); $^{31}$ {$^1$H} NMR (121 MHz, CDCl$_3$) δ=−48.9 (br s); $^{31}$P NMR (121 MHz, CDCl$_3$): δ=−48.9 (br d, $J_{PH}$=360 Hz); IR (nujol): ν(B-H)=2414, 2372 cm$^{-1}$, ν (P-H)=2200 cm$^{-1}$: elemental analysis calcd for C$_6$H$_8$BP: C, 59.1; H, 6.6; found: C, 58.9; H 6.5.

Figure 2:
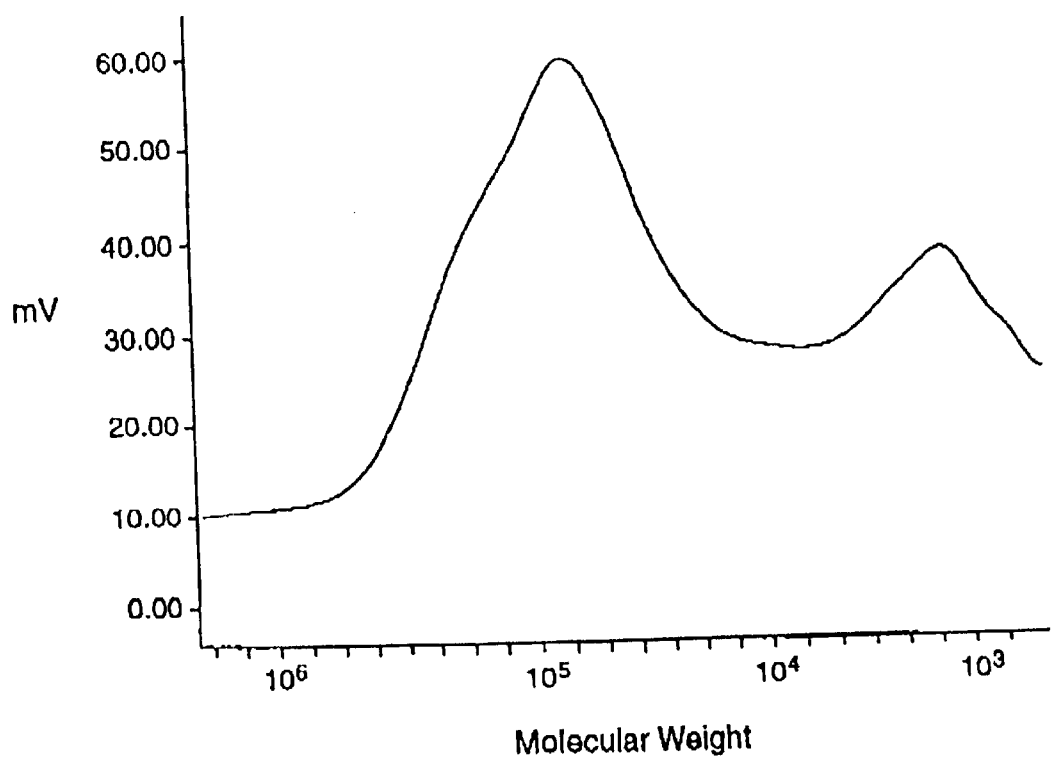
FIG. 2 represents a Gel Permeation Chromatogram for poly(phenylphosphinoborane) (III) in tetrahydrofuran using Polystyrene Standards.

Thus, the $^{31}$P NMR spectrum of 2 showed a broad singlet centered around—48.9 ppm which split into a doublet ($J_{PH}$=360 Hz) in the $^1$H coupled spectrum and is characteristic of a single hydrogen substituent at phosphorus (FIG. 2). The $^1$H NMR spectrum of (III) was also consistent with the assigned structure with broad peaks assigned to phenyl group (at 6.65–7.90 ppm) and BH$_2$ protons (at 0.67–2.19 ppm) and a broad doublet resonance centered at 4.25 ppm ($J_{PH}$=360 Hz) for the PH group. The $^{11}$B NMR spectrum of (III) showed a single broad resonance at −34.7 ppm which is characteristic for a 4-coordinate boron center attached to two phosphorus atoms. The molecular weight distribution of (III) was analyzed by Gel Permeation Chromatography (GPC) in THF and was shown to be bimodal (FIG. 2). The major, high molecular weight fraction corresponded to an apparent weight average molecular weight ($M_w$) of 115,820, an apparent weight average molecular weight ($M_n$) of 74,470, and a polydispersity index (PDI=$M_w$/$M_n$) of 1.55. The second, minor GPC fraction comprised low molecular weight oligomers ($M_n$=ca. 1,000). Further characterization of (III), which is air and moisture stable, was achieved by $^{13}$C NMR, IR spectroscopy, and elemental analysis which afforded data consistent with the assigned structure.

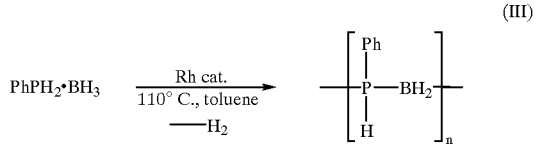

(III)

In contrast to the situation for Ph$_2$PH.BH$_3$, the dehydrocoupling of PhPH$_2$.BH$_3$ proceeds at a similar temperature in the absence of added catalyst. However, the rate is substantially slower and the observed molecular weights were considerably lower which indicates that P—B chain formation is much less efficient than in the catalyzed process (8). Experiments show that the dehydrocoupling reaction to form (III) can also be performed in the melt and substantially higher molecular weights have been obtained.

EXAMPLE 4
Synthesis of [PhPH—BH$_2$]$_n$ (III) in toluene

In a series of experiments using ca. 0.1–1 mol % [Rh(1,5-cod)$_2$][OTf] as catalyst, the molecular weights of the poly(phenyl phosphinoborane) formed varied in the range apparent $M_w$=80,000–150,000 and $M_n$=50,000–90,000. In the largest scale preparation PhPH$_2$.BH$_3$ (1.03 g, 8.27 mmol) and [Rh(1,5-cod)$_2$][OTf] (ca. 3 mg, 0.1 mol %) were dissolved in toluene (15 mL) and the resulting solution was refluxed for 14 h. The reaction mixture was then concentrated under vacuum to ca. 5 mL, filtered and precipitated into 120 mL of hexanes. The white polymeric product was washed with hexanes, decanted and dried in vacuo at 45° C. Yield 0.68 g (67%).

GPC (THF): apparent $M_w$=87,270, $M_n$=59,970, PDI=1.46; $^1$H NMR (300 MHz, CDCl$_3$): δ=6.65–7.90 (br, Ph), 4.25 (br d, $J_{PH}$=360 Hz, PH), 0.67–2.19 (br, BH$_2$); $^{11}$B{$^1$H} NMR (160 MHz, CDCl$_3$): δ=−34.7 (br, s); $^{13}$C{$^1$H} NMR (75 MHz, CDCl$_3$); δ=132.5 (br, m-Ph), 129.3 (br, p-Ph), 128.2 (br, o-Ph); ); $^{31}$ {$^1$H} NMR (121 MHz, CDCl$_3$) δ=−48.9 (br s); $^{31}$P NMR (121 MHz, CDCl$_3$): δ=−48.9 (br d, $J_{PH}$=360 Hz); IR (nujol): ν(B—H)=2414, 2372 cm$^{-1}$, ν(P—H)=2212 cm$^1$: elemental analysis calcd for C$_6$H$_8$BP: C, 59.1; H, 6.6; found: C, 58.9; H, 6.5.

EXAMPLE 5
Synthesis of High Molecular Weight [PhPH—BH2]$_n$ without Solvent

Neat PhPH$_2$.BH$_3$ (4.10 g, 33.1 mmol) and [Rh(μ-C1)1,5-cod)}$_2$] (ca. 50 mg, 0.6 mol % rhodium) were stirred for 3 h at 90° C. and then for 3 h at 130° C. When the temperature reached 130° C., vigorous gas elimination was observed and after 3 h the contents of the flask was completely solid. After cooling to room temperature, the dark yellow material was dissolved in THF (40 mL), filtered and precipitated into hexane (700 mL). The off-white polymeric product was washed with hexane, decanted and dried under vacuum at 50° C. for 48 h. Yield 3.03 g (75%).

Figure 3:
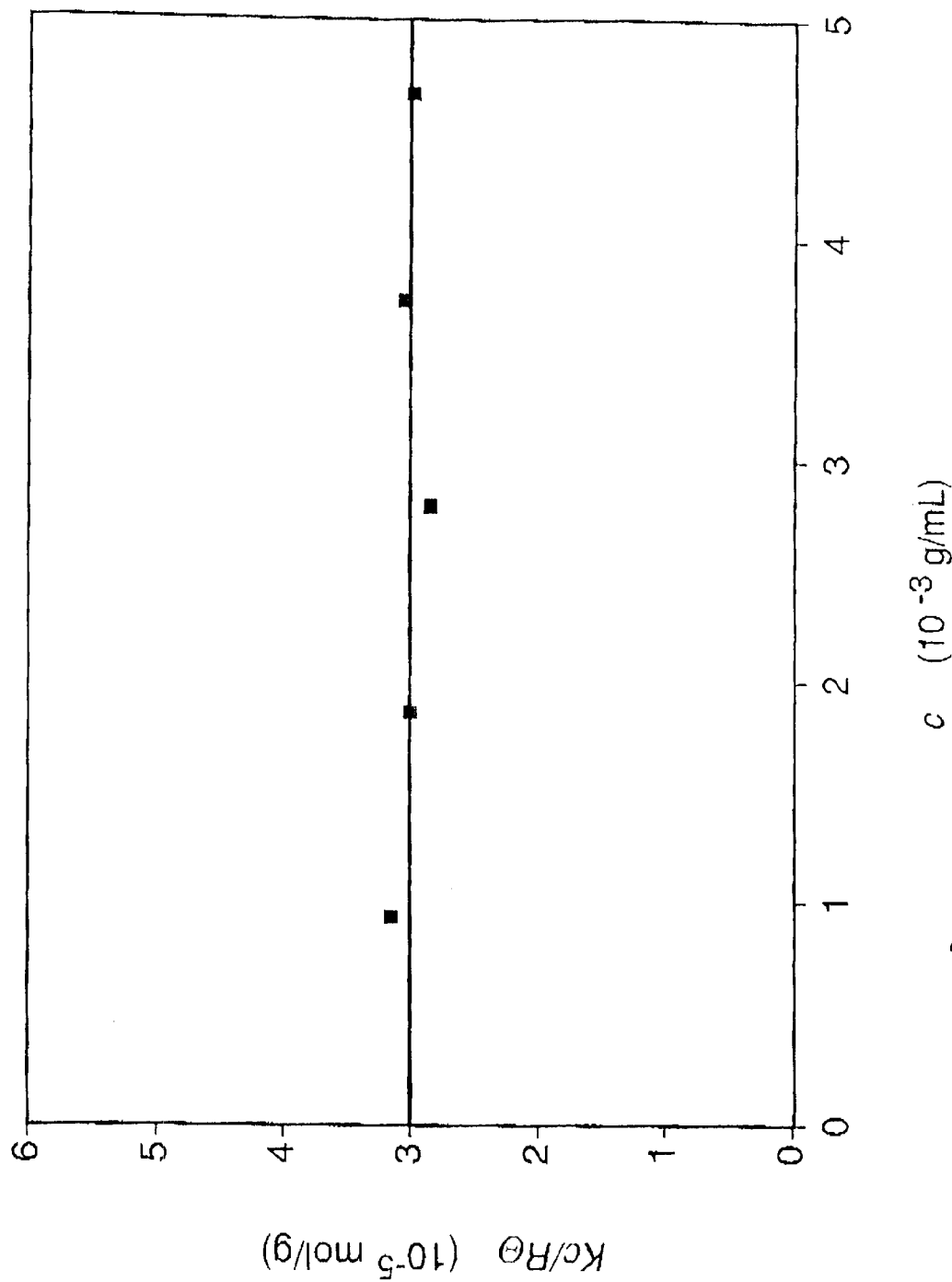
FIG. 3 represents a low-angle laser light scattering plot for high molecular weight [PhPH—BH$_2$]$_n$ in THF at 22° C. (k=optical constant, c=concentration, R$\theta$=Rayleigh ratio). The absolute molecular weight M$_w$ is determined as the inverse of the intercept on the y axis (M$_w$=33,300).

The $^1$H, $^{11}$B, $^{13}$C and $^{31}$P NMR and IR spectra are as described previously. Static light scattering (THF): absolute $M_w$=33,300, $DP_w$=273 (see FIG. 3).

A second polymerization was conducted following the same procedure wherein: 1.22 g PhPH$_2$.BH$_3$. (9.84 mmol) and ca. 1,5 mg [{Rh(m-C1)(1,5-cod)}2] (0.6 mol % rhodium) gave polymer 3 in 75% yield (0.90 g). Static light scattering (THF): absolute $M_w$=31,000, $DP_w$=254.

EXAMPLE 6
Synthesis of [PhP(n-Bu)—BH$_2$]$_n$

Poly(phenylphosphinoborane) (0.60 g, 4.92 mmol) was dissolved in dry THF (10 mL) and cooled to 0° C. A solution of 1 equiv n-butyllithium (3.08 mL, 1.6 M in n-hexane) or, alternatively, lithium diisopropylamide (1 equiv) and 2 equiv tetramethylethylenediamine (1.49 mL, 9.84 mmol) was then added dropwise. After stirring for 1 h at 0° C., excess butyl iodide (0.84 mL, 7.38 mmol) was added slowly. The reaction mixture was stirred overnight and precipitated into water (100 mL) and then into methanol (100 mL) from THF. The polymer was collected by filtration and dried overnight under vacuum at 45° C.

GPC (THF): $M_w$=49,527, $M_n$=42,664, PDI=1.16; $^{11}$B{$^1$H} NMR (160 MHz, CDCl$_3$): δ=−31.1 (br, s); $^{31}$P{$^1$H} NMR (121 MHz, CDCl$_3$) δ=−24.2 (br s). For lithium diisopropylamide reaction—absolute $M_w$~15,000 as measured by light scattering.

EXAMPLE 7
Synthesis of High Molecular Weight [iBuPH—BH$_2$]$_n$ without Solvent Neat iBuPH$_2$.BH$_3$ (0.45 g, 4.33 mmol) and [{Rh(μ-Cl)(1,5-cod)}$_2$] (ca. 11 mg, 1.0 mol % rhodium) were stirred for 13 h at 120° C. After cooling to room temperature, the sticky product was dissolved in THF (3 mL) and precipitated into isopropanol/water (40 mL/40 mL). The solution was decanted and the product redissolved in CH$_2$Cl$_2$ (3 mL). Removal of the volatiles under vacuum (50° C./24 h) left a light yellow sticky solid. Yield 0.35 g (80%). 1H NMR (300

MHz, CDCl$_3$): d=3.86 (br d, JHP=337 Hz, PH), 1.98 (m, CH), 1.51 (m, CH$_2$), 0.95 (d, JHH −5.5 Hz, CH$_3$), 0.8-2.0 (br, BH$_2$); $^{11}$B{1H} NMR (160 MHz, CDCl$_3$): d=−36.3 (br, n1/2 ca. 630 Hz); $^{13}$C{1H} NMR (75 MHz, CDCl$_3$): d=30,2 (d, JCP=29 Hz, CH), 25.6 (CH$_3$), 23.7 (CH$_2$); $^{31}$P{1H} NMR 121 MHz, CDCl$_3$) d=−69.2 (br, n1/2 ca. 300 Hz); IR (nujol): η(B—H) and η(P—H)=2421 (vs) cm-1; Anal. Calcd for C$_4$H$_{12}$BP: C, 47.1; H; 11.9. Found: C, 46.9; H 11.3. M$_w$ estimated as ca. 15,000 by light scattering.

RESULTS

The presence of about 0.3 mol % of the catalyst [Rh(1,5 cod)$_2$][OTf] with neat phosphine-borane adduct Ph$_2$PH BH$_3$ effects dehydrocoupling at 90°

A $^{31}$P NMR spectrum of the new compound showed the presence of 2 different phosphorus environments (δ=−3.3 and −17.7 ppm). Additional characterization by $^{11}$B and $^{1}$H NMR, mass spectrometry, and by single crystal X-ray diffraction (see FIG. 1) identified the product as the novel linear dimer 1. Notably, the P—B bonds in 1 (1.92–1.94 Å) are long compared to carbon-carbon bonds (ca. 1.54 Å) and have lengths typical of single bonds between four-coordinate phosphorus and boron centers.

The linear phosphorus-boron polymers according to the invention have utility as flame retardants per se, or in flame retardant compositions comprising said polymers.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

What is claimed is:

1. A method of producing a polymer having a linear backbone of alternating phosphorus and boron atoms, said method comprising dehydrocoupling a phosphine-borane adduct by treating said adduct at a temperature of less than 180° C. in the presence of an effective dehydrocoupling amount of a dehydrocoupling catalyst, to effect said dehydrocoupling to produce said polymer.

2. A method as defined in claim 1 wherein said catalyst is a transition metal catalyst selected from the group consisting of Rh, Ir, Ti, Ru, Pt and Pd.

3. A method as defined in claim 2 wherein said catalyst is selected from the group consisting of [Rh(1,5-cod)$_2$][OTf] and [{Rh(m-Cl)(1,5-cod)}2].

4. A polymer of the formula

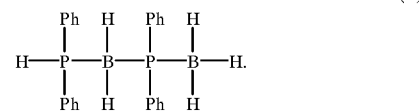

(II)

5. A fire retardant composition comprising a polymer as defined in claim 4.

* * * * *